(12) United States Patent
Neumetzler

(10) Patent No.: US 11,554,222 B2
(45) Date of Patent: *Jan. 17, 2023

(54) NEEDLE MODULE FOR A DRIVE-CONTROLLED APPARATUS FOR REPEATEDLY PIERCING HUMAN OR ANIMAL SKIN, AND HANDHELD UNIT

(71) Applicant: MT.DERM GmbH, Berlin (DE)

(72) Inventor: Heiko Neumetzler, Berlin (DE)

(73) Assignee: MT.DERM GMBH, Berlin (DE)

( * ) Notice: Subject to any disclaimer, the term of this patent is extended or adjusted under 35 U.S.C. 154(b) by 71 days.

This patent is subject to a terminal disclaimer.

(21) Appl. No.: 16/909,440

(22) Filed: Jun. 23, 2020

(65) Prior Publication Data

US 2020/0390980 A1 Dec. 17, 2020

Related U.S. Application Data

(63) Continuation of application No. 15/898,522, filed on Feb. 17, 2018, now Pat. No. 10,688,253.

(30) Foreign Application Priority Data

Feb. 17, 2017 (EP) .................................... 17156740

(51) Int. Cl.
  *A61M 5/32* (2006.01)
  *A61M 5/158* (2006.01)
  (Continued)

(52) U.S. Cl.
  CPC ......... *A61M 5/3221* (2013.01); *A01K 11/005* (2013.01); *A61M 5/158* (2013.01); *A61M 37/0076* (2013.01); *A61M 2005/1585* (2013.01)

(58) Field of Classification Search
  CPC .......... A61M 37/0076; A61M 37/0084; A61M 5/46; A61B 17/0469; A61B 17/0491;
  (Continued)

(56) References Cited

U.S. PATENT DOCUMENTS 8,029,527 B2 * 10/2011 Lisec ................ A61M 37/0076
  606/185
9,381,336 B2   7/2016 Jarling
  (Continued)

FOREIGN PATENT DOCUMENTS

DE  202010013095 U1  2/2011
DE  102014012896 A1  3/2016
  (Continued)

OTHER PUBLICATIONS

European Search Report for European Patent Application No. 17156740.7 dated Aug. 11, 2017. 3 pages.

*Primary Examiner* — Todd J Scherbel
(74) *Attorney, Agent, or Firm* — Leason Ellis LLP

(57) ABSTRACT

A needle module for a drive-controlled handheld unit for repeatedly piercing human or animal skin, comprising a housing; a needle holder, which can be moved back and forth in the housing in a longitudinal direction of the housing; a piercing device on the needle holder, which can be moved, on account of the movement of the needle holder, between a proximal and a distal position, in which a piercing tip of the piercing device is arranged outside the housing; a coupling component, which is coupled to the needle holder in such a way that a driving movement provided with a repetition frequency by a drive device that can be coupled to the coupling component can be introduced onto the needle holder; and a damping component, which is arranged between the needle holder and the coupling component and is configured to damp a transfer of force therebetween.

14 Claims, 12 Drawing Sheets

(51) Int. Cl.
*A01K 11/00* (2006.01)
*A61M 37/00* (2006.01)

(58) Field of Classification Search
CPC . A61B 17/06; A61B 17/06066; A61B 17/062; A61B 17/0625
See application file for complete search history.

(56) References Cited

U.S. PATENT DOCUMENTS

| | | | |
|---|---|---|---|
| 10,688,253 B2* | 6/2020 | Neumetzler | ......... A01K 11/005 |
| 2016/0263365 A1* | 9/2016 | Smith | ............... A61M 37/0076 |

FOREIGN PATENT DOCUMENTS

| | | | |
|---|---|---|---|
| EP | 2796164 A1 | 10/2014 |
| TW | 201406322 A1 | 2/2014 |

* cited by examiner

NEEDLE MODULE FOR A DRIVE-CONTROLLED APPARATUS FOR REPEATEDLY PIERCING HUMAN OR ANIMAL SKIN, AND HANDHELD UNIT

CROSS-REFERENCE TO RELATED APPLICATIONS

The present application is a continuation of U.S. application Ser. No. 15/898,522 filed Feb. 17, 2018 which claims priority to European Patent Application No. 17156740.7 filed on Feb. 17, 2017, which is hereby incorporated by reference in its respective entirety.

The invention relates to a needle module for a drive-controlled apparatus for repeatedly piercing human or animal skin, and to a handheld unit.

BACKGROUND

Apparatuses of this kind are used to locally pierce the skin, whereby a substance can then be introduced into the skin. For example, this substance can be a dye for producing a tattoo or can be permanent make-up. However, the introduction of a medical or a cosmetic substance via the skin can also be enabled in this way.

Handheld units that have a modular structure are known. Known handheld units have a drive module and a needle module coupled thereto, wherein the modules can be releasably connected. A drive device, for example a drive motor, is provided in a housing of the drive module. A driving force with a repetition frequency is thus provided by means of the drive device. The needle module coupled to the drive module has a piercing device, which can comprise a single needle or a group of needles. The piercing device is arranged on a needle holder, which can be moved back and forth in the housing of the needle module in the longitudinal direction. With the aid of a coupling mechanism, the driving force provided by the drive device is transferred from the drive device to the needle holder, so that the needle holder is moved back and forth with the piercing device during operation, whereby a piercing tip of the piercing device is arranged outside the housing of the needle module, at least in a distal position, and therefore the skin can be locally pierced.

Document DE 10 2014 012 896 A1 discloses an adapter with amplitude reduction for repeatedly piercing organic skin in order to introduce substances. The adapter has a first mass-spring system, consisting of an exchangeable drive-side coupling mechanism with a drive rod, which is guided slidingly in the axial bearings of the housing, and a spring element. The adapter also has a second mass-spring system, consisting of the spring elements, the spring block, the output rod, which is guided slidingly in the output-side axial bearings of the housing, and an exchangeable output-side coupling mechanism. The two spring systems are configured in such a way that a repetitive movement introduced into the drive side with a stroke X is converted with little loss into a smaller stroke Y on the output side.

In document DE 20 2010 013 095 U1, an apparatus for repeatedly piercing skin is described. The apparatus comprises a housing, a drive device, which is received in the housing and is configured to provide a driving force, a coupling mechanism, which is received in the housing, and a piercing device, which is coupled to the drive device by means of the coupling mechanism in such a way that the driving force is coupled by means of the coupling mechanism to the piercing device for a repeating piercing movement. Here, the piercing device comprises a base with a distal active surface formed thereon, with a plurality of spaced-apart piercing elements distributed over the active surface, wherein the base with the distal active surface formed thereon is mounted such that it can be tilted relative to the housing.

Document EP 2 796 164 A1 discloses a tattooing machine for introducing tattooing ink into human skin with the aid of a tattooing needle, which comprises a drive motor for driving the tattooing needle, a transmission unit, and a needle holder for accommodating the tattooing needle. The transmission unit converts a driving movement of the drive motor into a puncturing movement of the tattooing needle, causing said needle to penetrate the human skin. The transmission unit has a tilting lever, which in response to the driving movement of the drive motor performs a tilting movement. The tilting movement of the tilting lever actuates the tattooing needle into the puncturing movement. The tilting lever is connected via a bending spring to the needle holder. The stiffness of the bending spring is adjustable, and so the hardness of the puncturing movement can be varied.

Document TW 2014 06322 describes a machine for permanent eyebrow make-up. This machine comprises at least one machine body, a needle holder assembly, and a tattooing needle, and can also comprise a holding protection tube, a needle cover, and a needle cover protector for application.

SUMMARY

The object of the invention is to provide a needle module for a drive-controlled apparatus for repeatedly piercing human or animal skin, and also a handheld unit having improved operating properties.

The object is achieved by a needle module for a drive-controlled apparatus for repeatedly piercing human or animal skin and also by a handheld unit according to claims 1 and 14 respectively. Alternative embodiments are the subject of dependent claims.

In accordance with one aspect, a needle module for a drive-controlled apparatus for repeatedly piercing human or animal skin is provided. The needle module has a housing, in which a needle holder is arranged movably back and forth in longitudinal direction of the housing. A piercing device is arranged on the needle holder in such a way that the piercing device can be moved, on account of the movement of the needle holder, between a proximal position and a distal position, in which a piercing tip of the piercing device is arranged outside the housing. A coupling component is provided, which couples the needle holder in such a way that a driving movement provided with a repetition frequency by a drive device that can be coupled to the coupling component can be introduced onto the needle holder. A damping component is arranged between the needle holder and the coupling component, which damping device is configured to damp a transfer of force between the needle holder and the coupling component.

In accordance with a further aspect, a handheld unit for repeatedly piercing human or animal skin is provided which comprises a drive module comprising a drive device, by means of which a driving movement with a repetition frequency is provided. A needle module is connected to the drive module in such a way that the driving movement is coupled onto the needle holder with the piercing device.

The piercing device can be formed with one needle or a group of needles.

The drive device provides a driving movement that is not generated manually, but instead mechanically or in an automated manner. Here, the drive device can comprise an electric motor, for example.

The repetition frequency at which the driving movement is provided can be between approximately 40 and approximately 200 Hz.

The needle module can be provided as a disposable module. One or more components in the needle module can be produced from a plastic material, for example by means of injection moulding.

The coupling component can be provided in one or more pieces. Similarly, the housing of the needle module can be formed in one or more pieces, wherein, in the case that the housing is formed with a plurality of pieces, housing components can be releasably connected to one another.

The damping component can be connected to the coupling component and/or the needle holder by means of an interlocking connection.

An opening can be provided on the housing of the needle module in order to introduce a substance, which is to be applied to the skin, into the housing interior. Here, the substance can be introduced in a housing interior that is connected to a front-side module opening, which can also be referred to as a needle opening and through which the piercing device extends, at least in the distal position.

The distal position corresponds to an entirely or partially extended or forward-driven position of the needle holder with the piercing device. The piercing tip of the piercing device is then arranged outside the housing, so that the skin can be locally pierced. Here, the piercing device extends through a front-side opening of the housing of the needle module, which can also be referred to as a needle opening. By being moved back from the distal position, the needle holder and the piercing device arranged thereon are moved into a retracted position, which can be referred to as the proximal position and in which the piercing tip is set back in the direction of the needle module compared to the distal position, wherein the piercing tip can be arranged inside or outside the housing, for example inside the housing behind the front-side opening.

The damping component can be made of a resiliently yielding material. A resilient plastic material can be used. In this embodiment or other embodiments, the damping component can be formed in one or more pieces. For example, the damping component can be round or angled in cross-section in the various embodiments. In one embodiment, the damping component has a cylindrical shape.

Opposite end portions of the damping component can be directly coupled, respectively, one to the needle holder and one to the coupling component. The opposite end portions of the damping component can each be arranged in physical contact with the needle holder and the coupling component.

The damping component can be secured on the needle holder and/or the coupling component against a relative shifting, in particular transversely to the longitudinal direction of the housing. For this purpose, the damping component can be arranged on the needle holder and/or in the coupling component in an associated receptacle, for example an indentation on the needle holder and/or the coupling component. Alternatively or in addition, a protrusion can be formed on an end of the needle holder and/or the coupling component facing towards the damping component, which protrusion engages in an associated indentation on the damping component.

Damping provided by the damping component can be adjustable by means of an adjustment device. By means of the adjustment device, a degree of hardness of the damping and/or a length of the damping path can be adjusted, for example the extent of a compression or squeezing of the damping element under the pressure load at the ends.

On an inner wall of the housing, the adjustment device can comprise an adjustment component arranged movably on the needle holder and/or onto the coupling component. The adjustment component for example can limit a movement of the needle holder and/or of the coupling component, for example in that a stop is provided by the adjustment component, which stop is movable in order to thus adjust the damping. Alternatively or additionally, the adjustment component can be designed to restrict or limit a resilient deformation of the damping component.

The adjustment device can be designed to adjust a damping path. The damping path can determine the extent to which the damping component can be compressed or squeezed in the event of the damping. By moving the adjustment component, the damping path can be changed. Here, for example the adjustment component can provide a stop, the position of which relative to the needle holder and/or the coupling component is adjustable.

Alternatively or additionally, the adjustment device can be designed to limit a resilient deformation, for example a bulging as a result of resilient deformation, wherein the degree of the limitation can be adjustable.

The adjustment device can be operable from outside the housing in order to adjust the damping. A setting component can be provided which is accessible for operation from outside through a substance opening of the housing. For example, the setting component can be acted on by means of a screwdriver in order to move the adjustment element. Here or in other embodiments, the movement can be performed in the longitudinal direction of the needle holder. The substance opening can be a dye opening, which is designed to introduce a dye through said opening into the housing, which dye is to be applied to the skin. Other substances can also be applied by means of the apparatus, for example cosmetic or medical substances.

In one embodiment, alternatively or additionally, an adjustment mechanism to be actuated from outside the housing can be provided. Here, for example the adjustment component or element can be coupled by means of a thread to a setting component accessible from outside and a further setting component received in the housing, in such a way that as the setting component is rotated, the adjustment component is also rotated and on account of it being coupled to the further setting component by means of the thread is moved in the longitudinal direction of the needle holder, whereby an overlap with the damping component is adjusted. The damping component can be coupled at the rear side to the further setting component, which is coupled at the front side to the needle holder. The setting component can be actuatable, in particular rotatable, from outside through a housing opening. Alternatively, it can be provided that the further setting component with the thread is formed in one piece with the needle holder, so that in this case the thread is arranged on the needle holder, to which the damping component is coupled at the rear side.

The needle holder and the coupling component can be connected to one another by means of an associated component extension allowing a length reduction on account of the damping of the damping component. In this embodiment, the needle holder and coupling component are in direct contact in spite of the damping component arranged therebetween. For example, a telescopic extension can be provided, which shortens when compressive force is exerted onto the damping component, in particular when the piercing tip of the piercing device encounters the resistance of the skin as it is extended. In the case of the component extension, portions that slide into each other can be provided. Portions of the component extension can be formed on the needle holder and/or on the coupling component.

The component extension can extend along the damping component inside and/or outside said component. The component extension can extend in one embodiment through the damping component through an opening in the damping component. Alternatively or additionally, the component extension can be provided so as to surround the damping component externally at least in part.

In the housing, the needle holder and the damping component can be arranged in a piercing-side housing chamber and the coupling component can be arranged in a drive-side housing chamber, wherein the piercing-side and the drive-side housing chamber are separated by means of a membrane. The membrane, which is preferably formed of a resiliently yielding material, is received on the housing and can seal off the housing chambers with respect to one another. In one embodiment, it can be provided that the membrane extends from a drive-side end of the housing into the housing interior. The membrane can be provided as a closed membrane. Alternatively, the membrane can have a sealed opening, in order to enable therethrough the coupling between needle module and coupling component. Starting from the membrane opening, the coupling component can extend at the rear side towards the drive side, which in this embodiment or other embodiments is arranged, in turn, still completely or only partially within the housing. In one embodiment, a drive-side end of the coupling component can protrude at the rear side from the housing of the needle module in a starting position, which corresponds to the proximal position of the needle holder. A drive-side end of the damping component can be inserted into the membrane opening. Here, it can be provided that the drive-side end of the damping component then also extends into an associated holder on the piercing-side end of the coupling component, which faces the needle holder with the piercing device.

The damping component can be formed in one piece with the membrane. Such one-piece integral forming on the membrane can be provided for example by means of injection moulding, for example 2-component injection moulding. The integral forming can result in the formation of a sleeve portion, through which the coupling between needle holder and coupling component can be formed. The front region of the damping component can comprise an opening, into which the piercing device is inserted. The needle holder provided in alternative embodiments can be spared as a result. This function is performed by the damping component.

The damping component can be formed as a front-side extension of the membrane.

A piercing-side end of the coupling component can be arranged on a membrane opening. The membrane can extend in longitudinal direction of the housing and in a manner encompassing the coupling component. The membrane can be formed here with a pot shape.

The damping component can be formed in one piece with the needle holder. Here, the needle holder can be made of a resilient material, for example an elastomer.

The embodiments explained above in conjunction with the needle module can be provided accordingly in the case of the handheld unit for repeatedly piercing human or animal skin.

DESCRIPTION OF EXEMPLARY EMBODIMENTS

Further exemplary embodiments will be explained in greater detail hereinafter with reference to figures of a drawing, in which.

Figure 1:
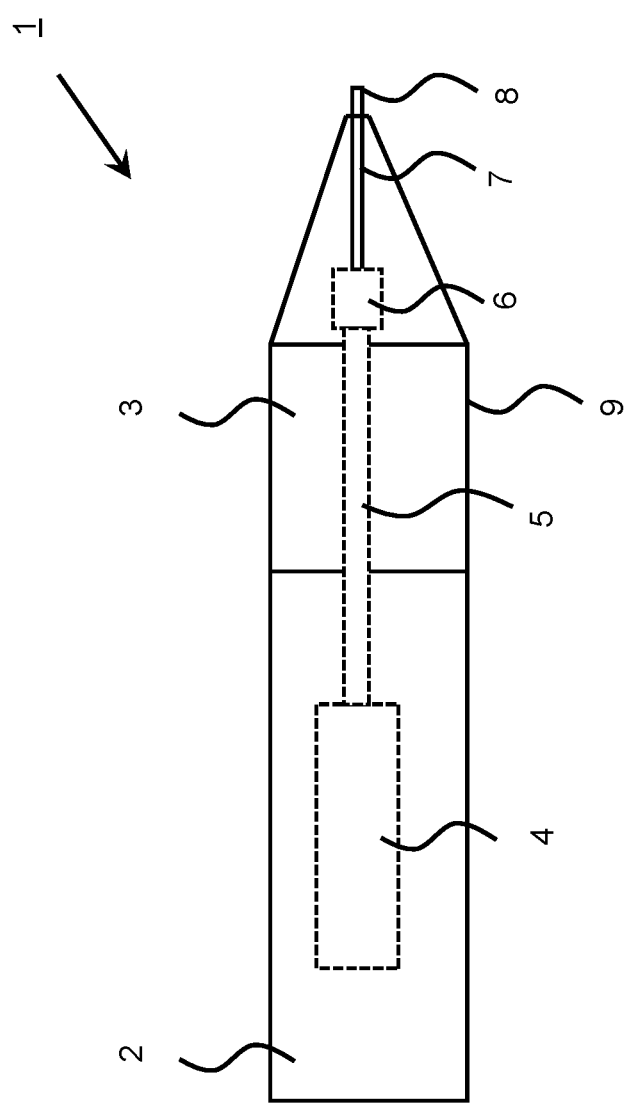
FIG. 1 shows a schematic illustration of a handheld unit for repeatedly piercing human or animal skin, with a needle module and a drive module.

FIG. 1 shows a schematic illustration of a handheld unit 1 for repeatedly piercing human or animal skin. The handheld unit 1 comprises a drive module 2 and a needle module 3 coupled thereto. A drive device 4, for example an electric motor, which is designed to provide a driving force or movement with a repetition frequency, which driving force or movement is transferred by means of a coupling mechanism 5 to functional components 6 in the needle module 3, is accommodated in the drive module 2.

In response to the coupled driving movement, a piercing device 7 is moved back and forth, so that a piercing tip 8 of the piercing device 7 is arranged outside a housing 9 of the needle module 3, at least in a distal position (see FIG. 1).

Hereinafter, embodiments for the needle module 3 will be further explained with reference to FIGS. 2 to 10. Here, the same reference signs are used for the same features.

Figure 2:
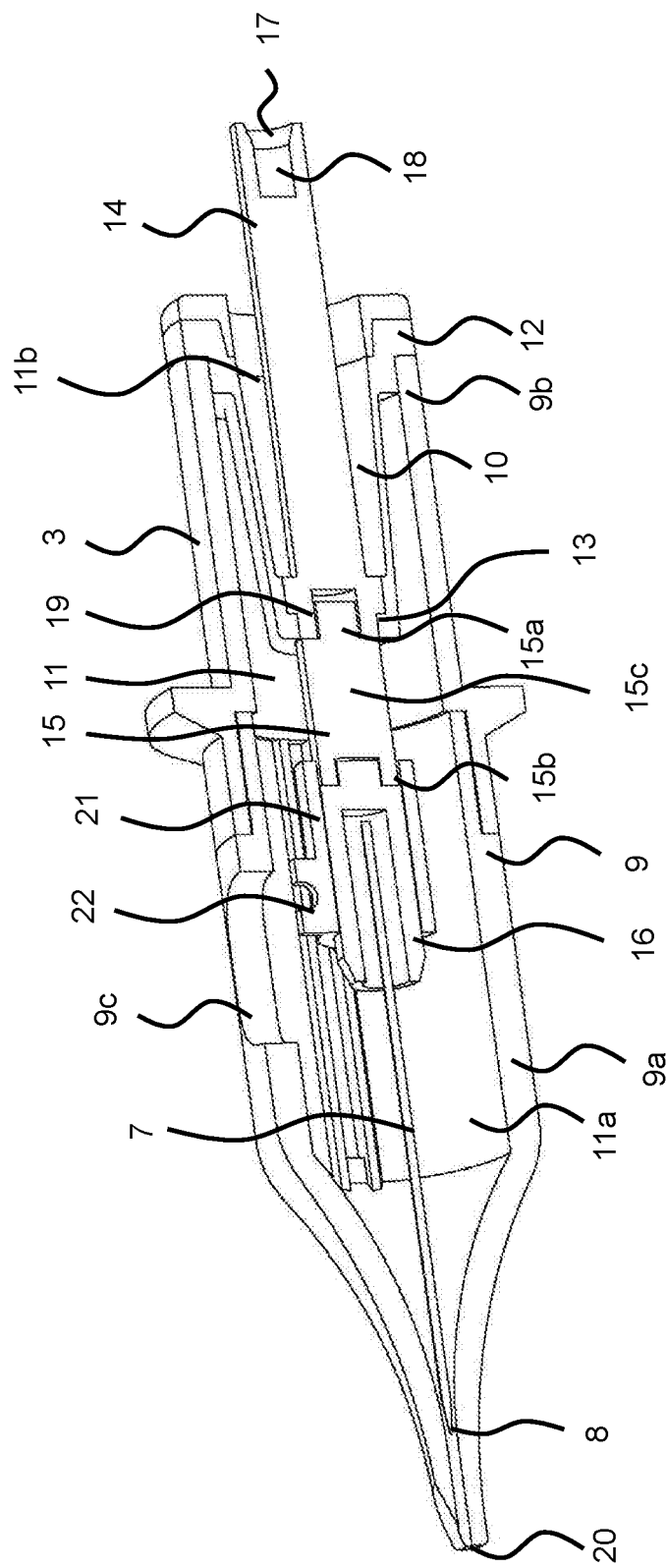
FIG. 2 shows a perspective illustration of a needle module in section.

FIG. 2 shows a perspective illustration of an embodiment of the needle module 3 in cross-section. The housing 9 has a front-side or piercing-side housing part 9a and a rear-side or drive-side housing part 9b, which are connected to one another releasably or non-releasably. A housing interior 11 is divided with the aid of a resilient membrane 10 into a piercing-side housing chamber 11a and a drive-side housing chamber 11b. The resilient membrane 10 seals off the two housing chambers 11a, 11b relative to one another, so that a passage of liquids or substances from the piercing-side housing chamber 11a into the drive-side housing chamber 11b is prevented. In the shown embodiment, the resilient membrane 10 in cross-section has a pot shape and extends in portions in the longitudinal direction of the housing 9. The resilient membrane 10 is fixed peripherally in a sealing manner on a drive-side end 12 of the housing 9.

In the shown embodiment, the resilient membrane 10 has a membrane opening 13, at the rear side of which there is arranged a coupling component 14, wherein, in the shown embodiment, an interlocking connection is produced by way of example. The coupling component 14 is used to introduce a driving movement, provided with a repetition frequency by the drive device 4 in the drive module 2, onto a needle holder 16, which is arranged movably in the longitudinal direction in the housing 9, via a damping component 15. For coupling to the drive device 4, the coupling component 14 has a holder 18 on a drive-side end 17.

A front holder 19, into which a drive-side end 15a of the damping component 15 is inserted, for example so as to form an interlocking connection, is provided on the coupling component 14 on the piercing side. The drive-side end 15a of the damping component 15 passes through the membrane opening 13 in the shown exemplary embodiment. A piercing-side end 15b of the damping component 15 is supported in an interlocking manner on the needle holder 16.

The piercing device 7, which can be an individual needle or a group of needles, is arranged on the needle holder 16.

In a middle part 15c, the damping component 15 can be squeezed resiliently and in so doing can increase its diameter (see FIGS. 6 and 7 below).

As a result of the driving movement or force introduced onto the needle holder 16, the piercing device 7 is moved back and forth through a front-side opening 20 on the housing 9, in such a way that the needle holder 16 and the piercing device 7 arranged thereon are moved between a proximal position (see FIG. 2) and a distal position (see FIGS. 5 to 7), in which the piercing tip 8 is arranged outside the housing 9 and protruding from the front-side opening 20.

Figure 3:
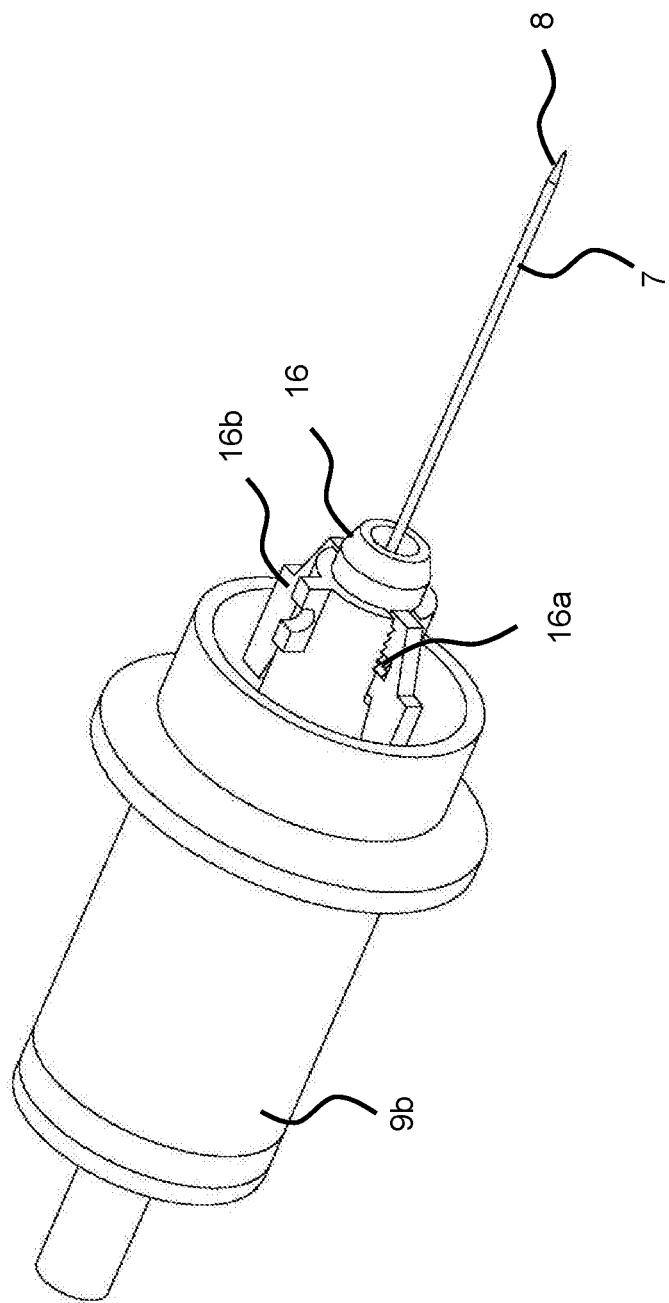
FIG. 3 shows a perspective illustration of part of the needle module from FIG. 2.
Figure 4:
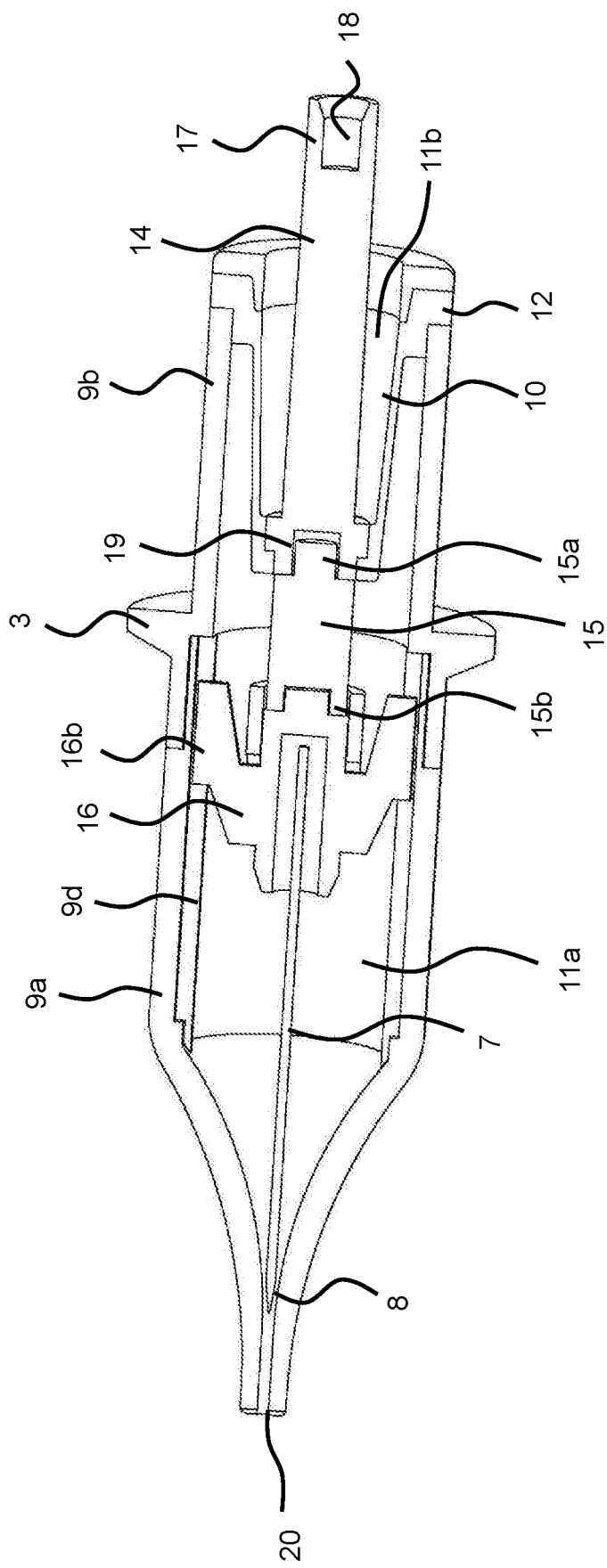
FIG. 4 shows a further schematic illustration of the needle module from FIG. 1 in section.

FIG. 3 shows a perspective illustration of elements of the needle module from FIG. 2, wherein the front and the rear housing part 9a, 9b are separated.

Figure 5:
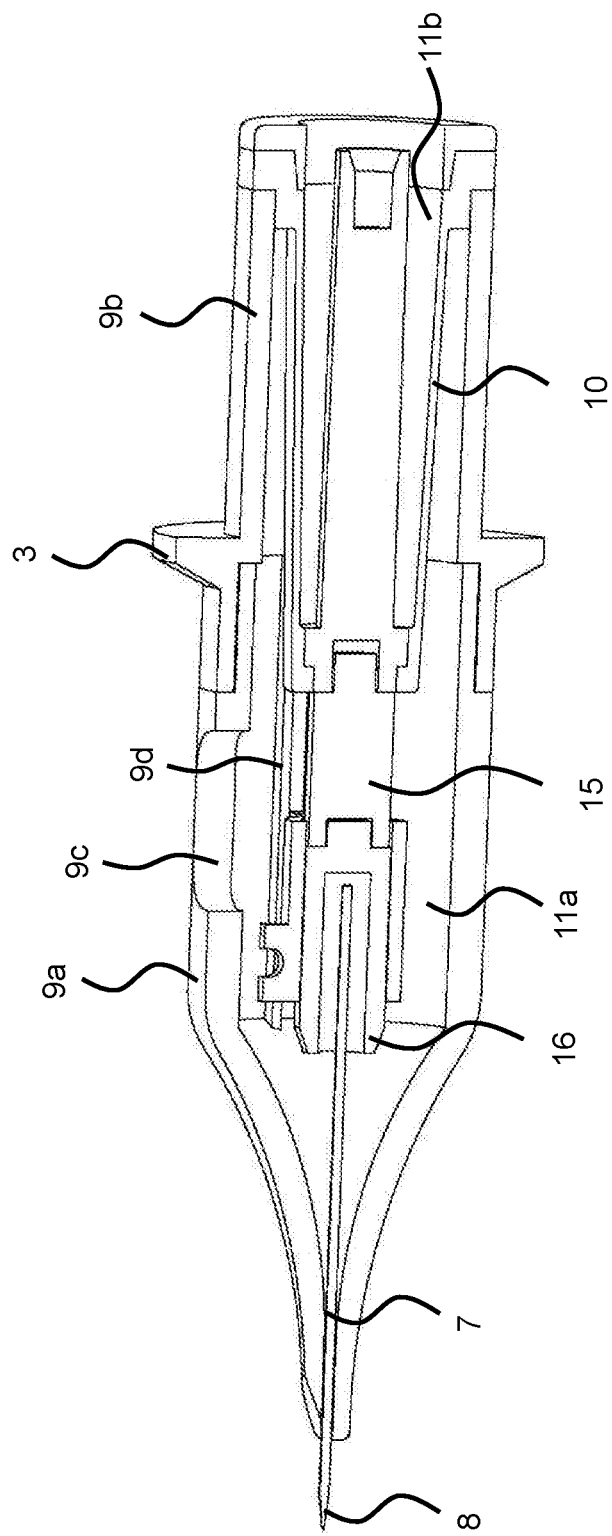
FIG. 5 shows a further perspective illustration of the needle module from FIG. 1 in the state without any load on the piercing device.
Figure 6:
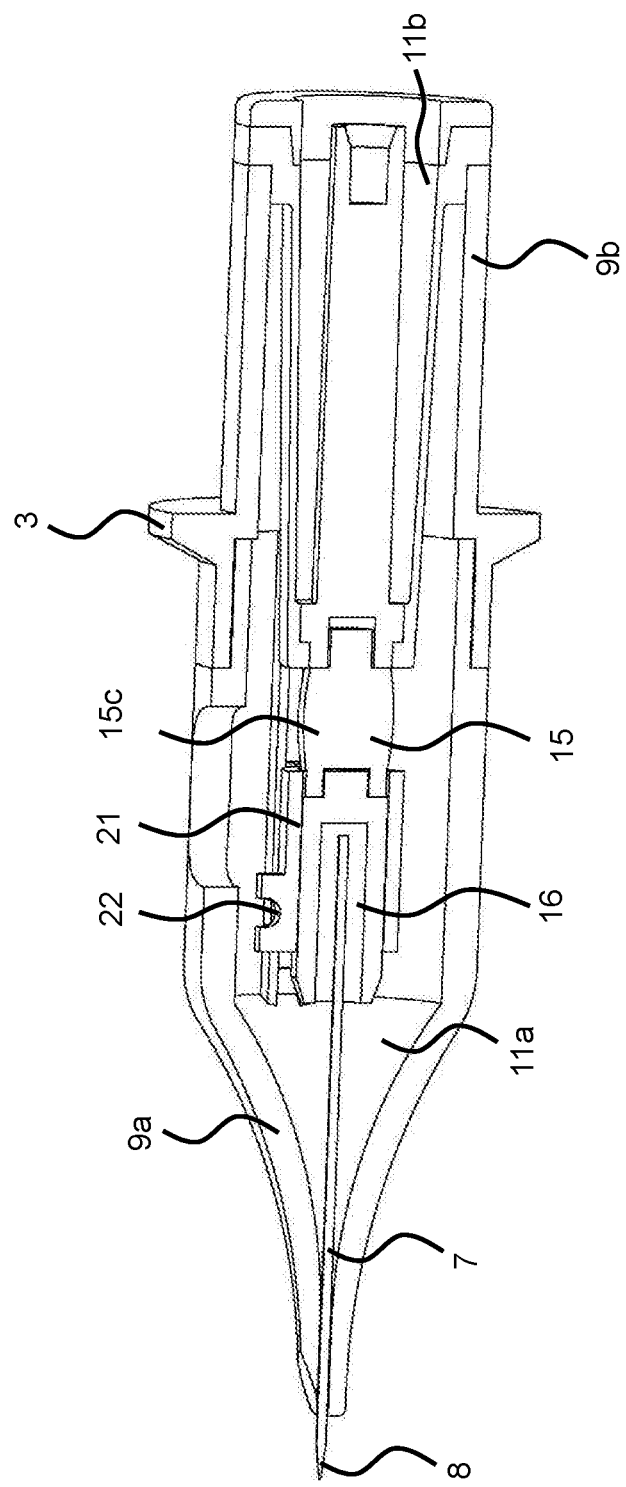
FIG. 6 shows a perspective illustration of the needle module from FIG. 1 in the state with a load on the piercing device.

FIGS. 4 to 7 show perspective illustrations of the needle module 2 from FIG. 1. The illustrations in FIGS. 4 and 5 relate to the state in which there is no load on the piercing device 7. FIG. 6 shows the state of a partially resiliently squeezed damping component 15, which is the result of a pressure or a load on the piercing tip 8, for example when this contacts the skin that is to be pierced. The damping component 15 then realises its damping effect.

Figure 7:
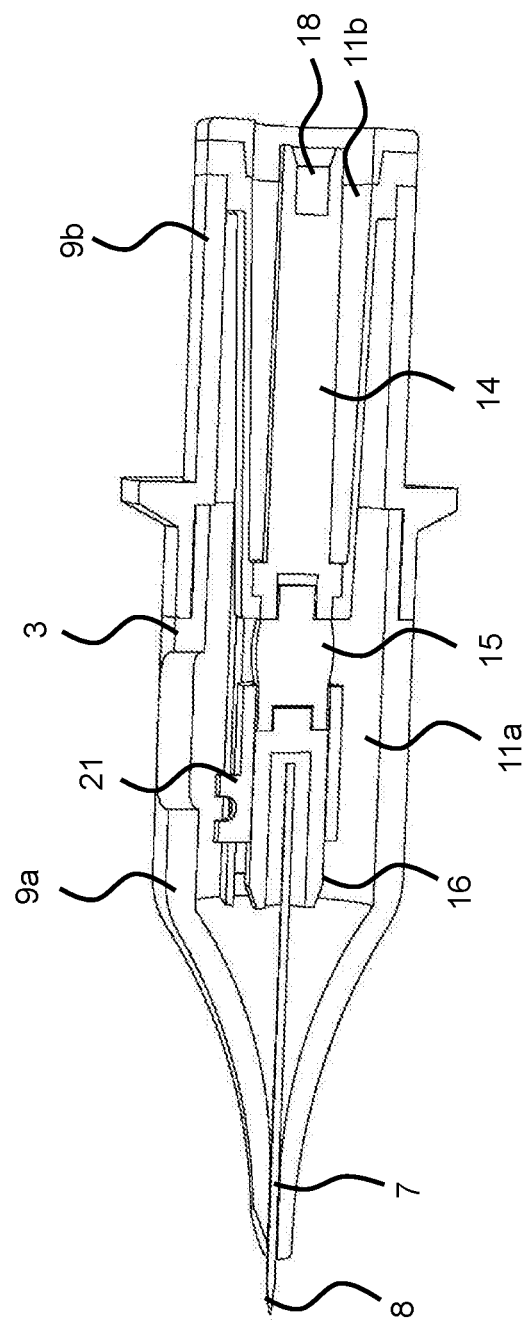
FIG. 7 shows a further perspective illustration of the needle module from FIG. 1 in the state with a load on the piercing device with harder damping adjustment.

In the illustration in FIG. 7, a harder damping adjustment has been selected for the damping component 15 in that an adjustment component 21, which is arranged movably on the needle holder 16, has been displaced in the direction of the coupling component 14, in such a way that an overlap between the adjustment component 21 and the damping component 15 is increased. As a result, a resilient compression of the damping component 15 can be limited. The adjustment component 21 can be secured in the various positions, for example by means of a catch connection 16a or a screw. An embodiment with an adjustable catch connection is shown in FIG. 3.

For displacement, the adjustment component 21 has an adjustment portion 22, which can be acted on for example by means of a screwdriver in order to move the adjustment element 21. The adjustment portion 22 can be actuated through a further housing opening 9c.

According to FIG. 5, a guide 9d for the needle holder 16 is provided on the inside of the housing 9, wherein wings 16b are guided along the guide 9d.

Figure 8:
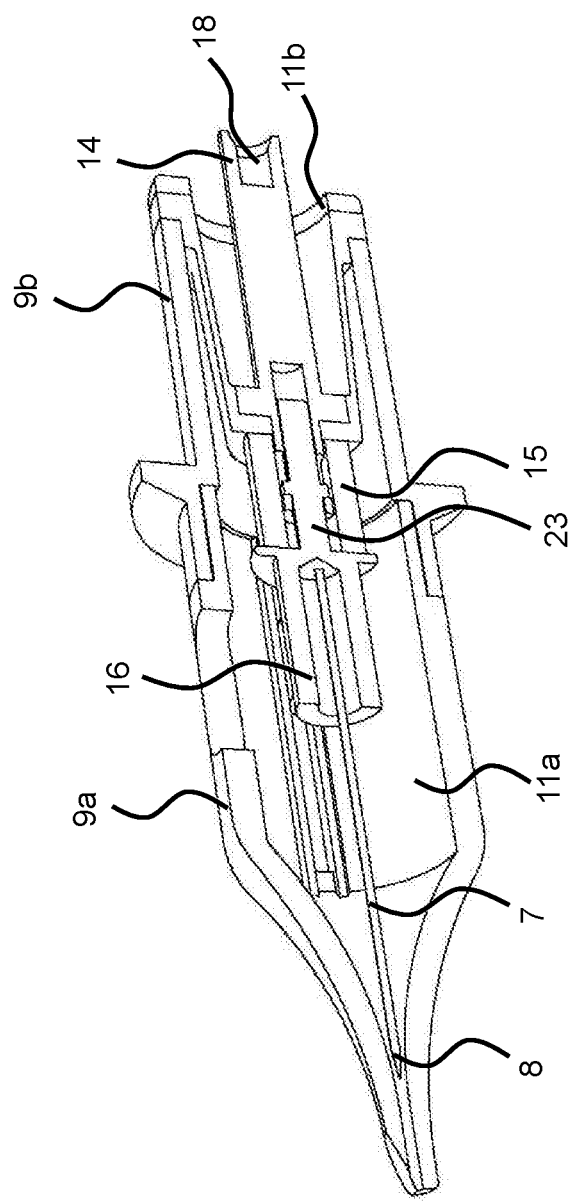
FIG. 8 shows a perspective illustration of another needle module.

FIG. 8 shows a perspective illustration of a further needle module 2, in which the needle holder 16 and the coupling component 14 are connected to one another by means of a component extension 23, which extends through the damping component 15. The component extension 23 is shortened in the event of a load on the piercing tip 8 of the piercing device 7, whereby the needle holder 16 and coupling component 14 are brought closer to one another, wherein this is damped by the damping component 15.

Figure 9:
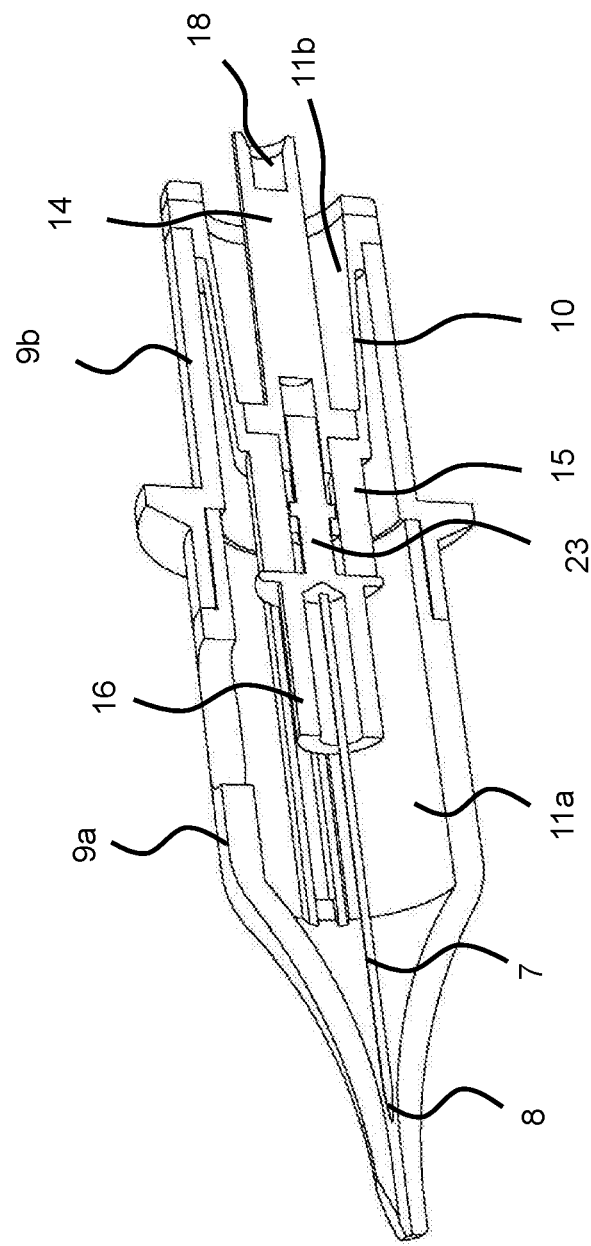
FIG. 9 shows a perspective illustration of a further needle module.

In the embodiment in FIG. 9, the damping component 15 is formed in one piece with the membrane 10. The damping component 15 is formed as a front-side extension of the membrane 10.

In the exemplary embodiments from FIGS. 8 and 9 as well, an adjustability of the degree of damping can be provided, for example similar to the adjustment component 21.

Figure 10:
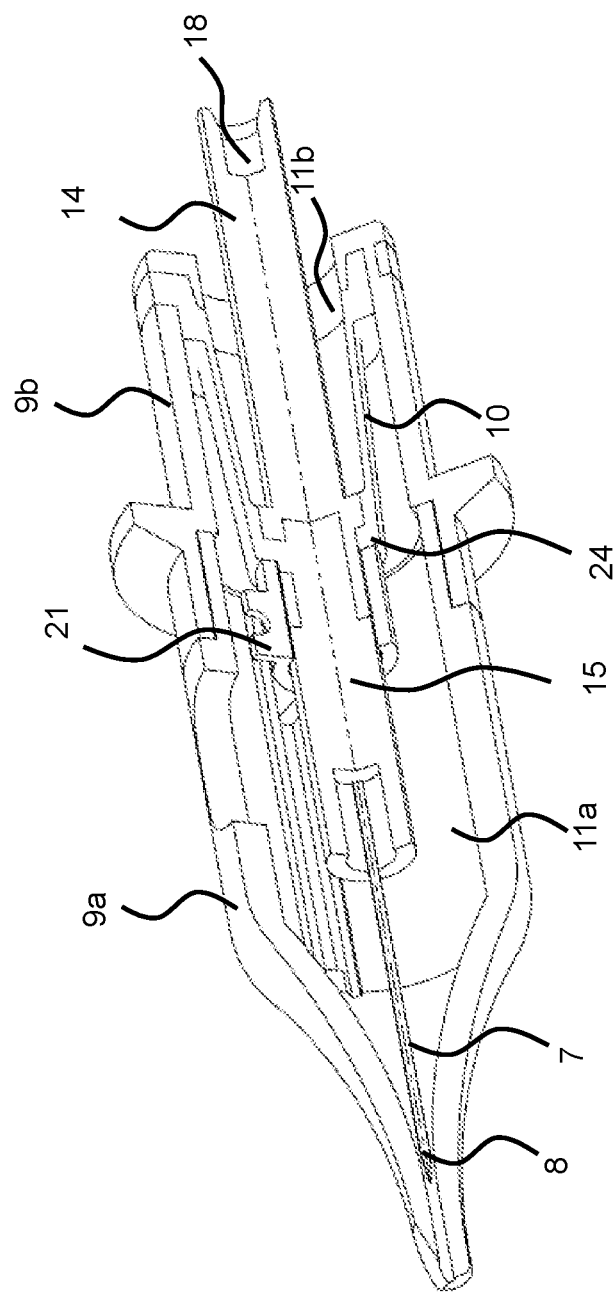
FIG. 10 shows a perspective illustration of a further needle module with adjustable degree of damping.

FIG. 10 shows a perspective illustration of a further needle module 2 with adjustable degree of damping. The adjustment component 21 overlaps with the damping component 15, which in this embodiment is formed in one piece with the membrane 10 and is integrally moulded in an interlocking manner on the coupling component 14, for example by means of 2-component injection moulding. The front region of the damping component 15 has an opening, into which the piercing device 7 is inserted. The needle holder 16 provided in alternative embodiments is spared as a result. This function is performed by the damping component 15.

Figure 11:
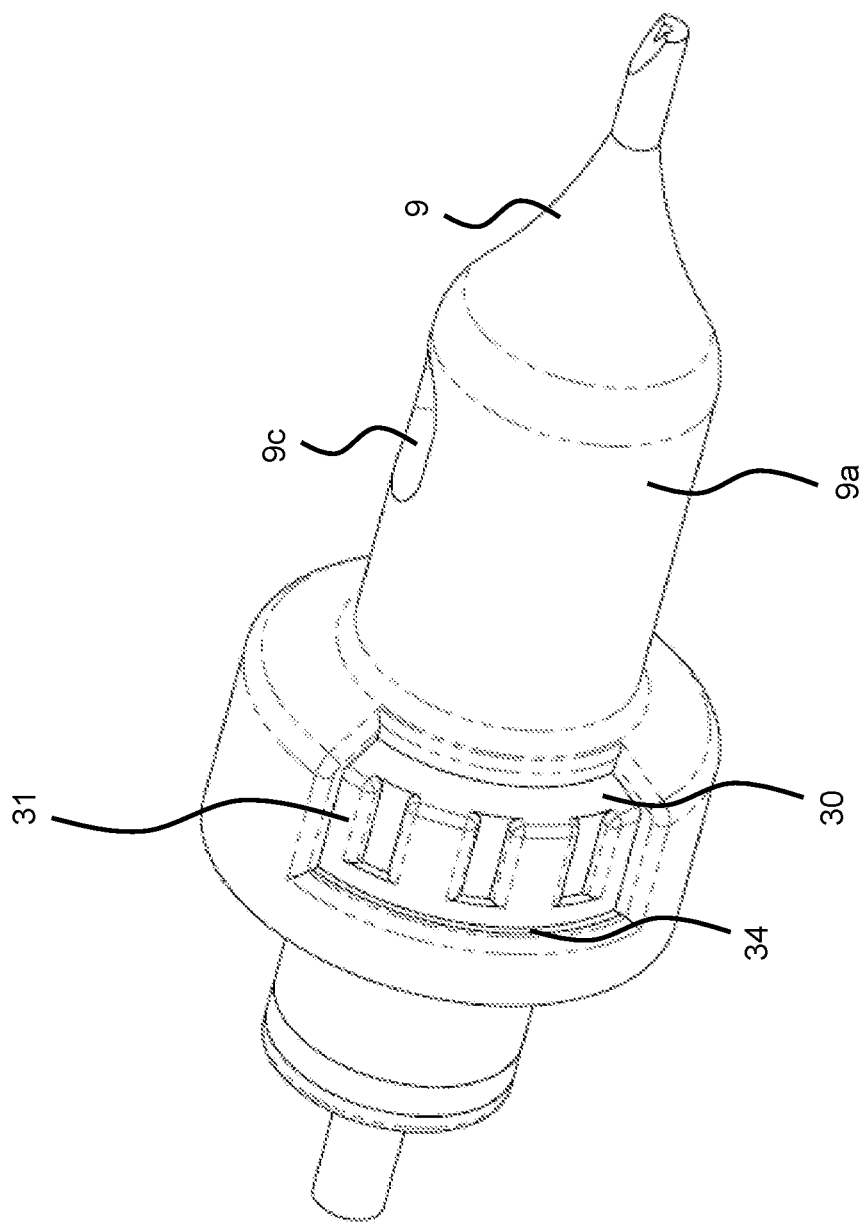
FIG. 11 shows a perspective illustration of another needle module with adjustable degree of damping.
Figure 12:
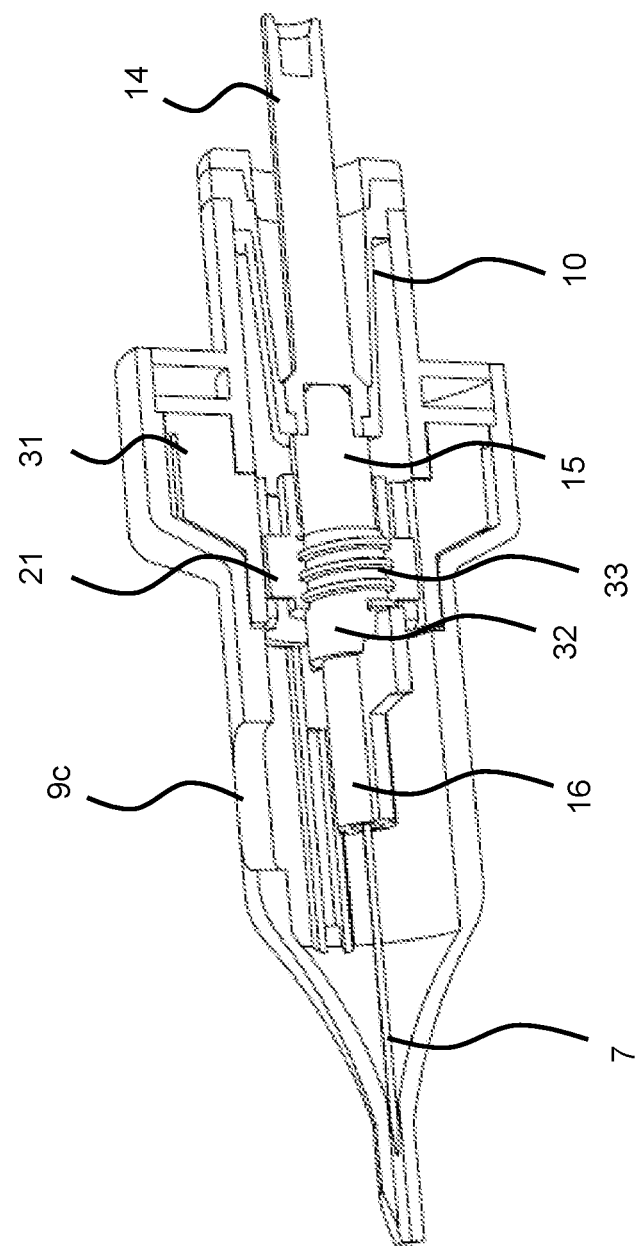
FIG. 12 shows an illustration of the other needle module from FIG. 11 in section.

FIGS. 11 and 12 show a perspective illustration and a sectional illustration of another needle module 2 with adjustable degree of damping. An adjustment mechanism 30 that is to be actuated from outside is provided, in which the adjustment component 21 is coupled to a setting component 13, which is accessible from outside and is embodied as a control wheel, and to a further setting component 32, which is accommodated in the housing 9, by means of a thread 33 in such a way that, as the setting component 31 rotates, the adjustment component 21 is also rotated and on account of its coupling to the further setting component part 32 by means of the thread 33 is moved in the longitudinal direction, whereby an overlap with the damping component 15 is adjusted. The damping component 15 here is coupled at the rear side to the further setting component 32, which at the front side is coupled to the needle holder 16.

It can be provided that the further setting component 32 is formed in one piece with the needle holder 16, so that in this case the thread 33 is arranged on the needle holder 16, to which the damping component 15 is coupled at the rear side.

The setting component 31 can be actuated, in particular can be rotated, from outside via a housing opening 34.

The features disclosed in the above description, the claims and the drawing can be of significance either individually or in any combination for the implementation of the various embodiments.

The invention claimed is:

1. A needle module for a drive-controlled handheld unit for repeatedly piercing human or animal skin, comprising:
   a housing;
   a needle holder, which is arranged in the housing such that it can be moved back and forth in a longitudinal direction of the housing;
   a piercing device, which is arranged on the needle holder in such a way that the piercing device can be moved, on account of the movement of the needle holder, between a proximal and a distal position, in which a piercing tip of the piercing device is arranged outside the housing;
   a coupling component, which is coupled to the needle holder in such a way that a driving movement provided with a repetition frequency by a drive device that can be coupled to the coupling component can be introduced onto the needle holder; and a damping component, which is arranged between the needle holder and the coupling component and is configured to damp a transfer of force therebetween, wherein the damping component is secured on the coupling component against shifting transversely to the longitudinal direction of the housing, wherein the damping provided by the damping component can be adjusted by means of an adjustment device.

2. The needle module according to claim 1 wherein, the damping component is made of a resiliently yielding material.

3. The needle module according to claim 1, wherein opposite end portions of the damping component are directly coupled, respectively, one to the needle holder and one to the coupling component.

4. The needle module according to claim 1, wherein the needle holder and the coupling component are connected to one another by means of an associated component extension allowing a length reduction on account of the damping of the damping component.

5. The needle module according to claim 4, wherein the component extension extends along the damping component inside and/or outside said damping component.

6. The needle module according to claim 1, wherein the housing, the needle holder and the damping component are arranged in a piercing-side housing chamber and the coupling component is arranged in a drive-side housing chamber, wherein the piercing-side and the drive-side housing chambers are separated by means of a membrane.

7. The needle module according to claim 6, wherein the damping component is formed in one piece with the membrane.

8. The needle module according to claim 6, wherein a piercing-side end of the coupling component is arranged on a membrane opening.

9. The needle module according to claim 6, wherein the membrane extends in the longitudinal direction of the housing and in a manner encompassing the coupling component.

10. A needle module for a drive-controlled handheld unit for repeatedly piercing human or animal skin, comprising:
    a housing;
    a needle holder, which is arranged in the housing such that it can be moved back and forth in a longitudinal direction of the housing;
    a piercing device, which is arranged on the needle holder in such a way that the piercing device can be moved, on account of the movement of the needle holder, between a proximal and a distal position, in which a piercing tip of the piercing device is arranged outside the housing;
    a coupling component, which is coupled to the needle holder in such a way that a driving movement provided with a repetition frequency by a drive device that can be coupled to the coupling component can be introduced onto the needle holder;
    and
    a damping component, which is arranged between the needle holder and the coupling component and is configured to damp a transfer of force therebetween, wherein the damping provided by the damping component can be adjusted by means of an adjustment device.

11. The needle module according to claim 10, wherein the adjustment device has an adjustment component arranged movably on an inner wall of the housing, on the needle holder and/or on the coupling component.

12. The needle module according to claim 10, wherein the adjustment device is designed to adjust a damping path.

13. The needle module according to claim 10, wherein the adjustment device can be operated from outside the housing and has an adjustment portion, which is accessible for operation from outside through a substance opening of the housing.

14. A handheld unit for repeatedly piercing human or animal skin, comprising
    a drive module, which has a drive device, by means of which a driving movement with a repetition frequency is provided; and
    a needle module, the needle module comprising:
        a housing;
        a needle holder, which is arranged in the housing such that it can be moved back and forth in a longitudinal direction of the housing;
        a piercing device, which is arranged on the needle holder in such a way that the piercing device can be moved, on account of the movement of the needle holder, between a proximal and a distal position, in which a piercing tip of the piercing device is arranged outside the housing;
        a coupling component, which is coupled to the needle holder in such a way that the driving movement provided with the repetition frequency by the drive device that can be coupled to the coupling component can be introduced onto the needle holder; and
        a damping component, which is arranged between the needle holder and the coupling component and is configured to damp a transfer of force therebetween, the damping component is secured on the coupling component against shifting transversely to the longitudinal direction of the housing, wherein the needle module is connected to the drive module in such a way that the driving movement is coupled onto the needle holder with the piercing device, wherein the damping provided by the damping component can be adjusted by means of an adjustment device.

* * * * *